United States Patent
Sidor, Jr. et al.

(10) Patent No.: US 6,482,214 B1
(45) Date of Patent: Nov. 19, 2002

(54) INTRAVASCULAR SEAL WITH MESH REINFORCEMENT AND METHOD FOR USING SAME

(75) Inventors: William E. Sidor, Jr., Rockford, MI (US); Carolyn Bocheff, Grand Haven, MI (US); John D. Hall, Belmont, MI (US); Gregory Marini, Solon Township, MI (US); Jack Goodman, Ann Arbor, MI (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/559,471

(22) Filed: Apr. 27, 2000

(51) Int. Cl.[7] ............................................. A61B 17/04
(52) U.S. Cl. ........................ 606/151; 606/153; 606/213
(58) Field of Search ................................. 606/151, 153, 606/213

(56) References Cited

U.S. PATENT DOCUMENTS

| | | | |
|---|---|---|---|
| 4,710,192 A | 12/1987 | Liotta et al. .................... 623/1 |
| 4,852,568 A | 8/1989 | Kensey ........................ 128/325 |
| 5,258,000 A | * 11/1993 | Gianturco .................. 606/151 |
| 5,284,488 A | 2/1994 | Sideris ........................ 606/213 |
| 5,350,399 A | 9/1994 | Erlebacher et al. ......... 606/213 |
| 5,368,602 A | * 11/1994 | de la Torre ................ 606/151 |
| 5,383,897 A | 1/1995 | Wholey ....................... 606/213 |
| RE34,866 E | 2/1995 | Kensey et al. .............. 606/213 |
| 5,405,360 A | 4/1995 | Tovey ........................ 606/151 |
| 5,425,744 A | 6/1995 | Fagan et al. ................ 606/213 |
| 5,443,497 A | * 8/1995 | Venbrux ........................ 623/1 |
| 5,507,811 A | 4/1996 | Koike et al. ................. 623/11 |
| 5,620,461 A | * 4/1997 | De Moer et al. ........... 606/213 |
| 5,649,959 A | 7/1997 | Hannam et al. ............ 606/213 |
| 5,725,552 A | 3/1998 | Kotula et al. ............... 606/213 |
| 5,741,297 A | 4/1998 | Simon ........................ 606/213 |
| 5,797,960 A | 8/1998 | Stevens et al. ............. 606/213 |
| 5,879,366 A | 3/1999 | Shaw et al. ................. 606/213 |
| 5,904,703 A | 5/1999 | Gilson ........................ 606/213 |
| 5,954,767 A | 9/1999 | Pajotin et al. ................ 623/11 |
| 5,957,939 A | 9/1999 | Heaven et al. ............. 606/151 |
| 5,957,952 A | 9/1999 | Gershony et al. .......... 606/213 |
| 6,042,569 A | 3/2000 | Finch, Jr. et al. .......... 604/175 |
| 6,056,762 A | 5/2000 | Nash et al. ................. 606/153 |
| 6,152,945 A | 11/2000 | Bachinski et al. .......... 606/198 |
| 6,214,022 B1 | 4/2001 | Taylor et al. ............... 606/153 |

FOREIGN PATENT DOCUMENTS

WO     WO99/08603     2/1999

* cited by examiner

Primary Examiner—Gary Jackson
(74) Attorney, Agent, or Firm—Thomas G. Berry; Michael J. Jaro; Daniel W. Latham

(57) ABSTRACT

An intravascular device is provided. The device comprises a sealing member, the member including a mesh material and a gripping element operatively attached to the sealing member, the gripping element operatively adapted to allow a user to position the sealing member to seal a blood vessel. Methods of using the device are also provided.

17 Claims, 6 Drawing Sheets

INTRAVASCULAR SEAL WITH MESH REINFORCEMENT AND METHOD FOR USING SAME

FIELD OF THE INVENTION

This invention relates to intravascular devices for insertion into a blood vessel through an opening in the wall of the blood vessel. More particularly, this invention relates to intravascular devices incorporating a mesh reinforcement for structural integrity.

BACKGROUND OF THE INVENTION

Intravascular seals may be inserted into blood vessels in a variety of procedures that require formation of a connection (anastomosis) between a bypass graft and donor or recipient blood vessel. The seals may be used during the procedure to maintain vessel integrity while the procedure is occurring.

Typically, an occlusion assembly is provided for sealing puncture openings. After puncturing a blood vessel with a needle and introducer sheath and subsequent withdrawal of the needle, the occlusion device can be inserted into the vessel via the introducer sheath. The occlusion device comprises a device that is attached to a retaining element such as a thread. In the blood vessel, it unfolds to have a surface area, which is larger than the surface area of the puncture opening to be occluded.

Subsequently the introducer sheath is removed out of the opening in the vessel and by pulling the retaining thread, the sheet material of the occlusion element will come to lie against the inside of the blood vessel wall. Thereafter, a retainer ring is placed around the thread and engages with the outer surface of the blood vessel for a fixed positioning of the occluding device. The device, the thread and the retainer ring are made of bio-absorbable material such that it is ensured that after the opening in the blood vessel has been occluded, these parts will disappear, for example after a few weeks.

Another type of intravascular seal is described in WO99/08603, assigned to Medtronic, Inc. This seal may be inserted into and subsequently retrieved from a blood vessel through an opening in the wall of the vessel. After completion of the anastomosis, the seal can be retrieved from the recipient vessel. Upon retrieval the sheet material is folded when it is contacted by the sides of the opening in the vessel wall.

The above seals must be flexible in order to be inserted into the blood vessel properly. However, if the seals are too flexible, they may not maintain the desired shape to ensure sealing of the vessel. Additionally, if the gripping element of the seal is not an easily graspable mechanism, it may be difficult to remove the seal because the gripping element will slip out of the users hands. Moreover, if the seals are too flimsy, they may rip while being retrieved from the vessel, particularly in the segment where the gripping element is attached to the seal.

It would be desirable therefore to provide an intravascular seal with desired flexibility that still maintains its desired structural integrity.

It would also be desirable to provide an intravascular seal to which an easily graspable gripping element may be securely attached.

It would also be desirable to provide an intravascular seal that may be easily inserted and retrieved.

SUMMARY OF THE INVENTION

One aspect of the present invention provides an intravascular device. The device comprises a sealing member, the member including a mesh material and a gripping element operatively attached to the sealing member, the gripping element operatively adapted to allow a user to position the sealing member to seal a blood vessel. The mesh material may comprise a plurality of mesh strands. The gripping element may comprise a tether. The tether may be attached to at least one of the mesh strands. The mesh material may form a grid pattern that may be used to measure a length of an incision. The gripping element may be a tube with a channel formed therein and at least one thread contained within the channel. The sealing member may have an oval shape, may be curled to facilitate insertion into a blood vessel, may be thinner near its perimeter than near its center, may have increased stiffness along its length, may be made of a non-biodegradable material, may be made of a deformable sealing material, or may be foldable for placing the sealing member into an insertion configuration and unfoldable to contact a blood vessel wall in a sealing configuration.

Another aspect of the present invention provides a device for insertion into a blood vessel through an opening in the wall of the vessel. The device comprises a flexible sealing member adapted to fold into an insertion configuration, a mesh material integrated with the sealing member; and a gripping element operatively attached to the sealing member. The gripping element may be attached to the mesh material. The mesh material may comprise a plurality of mesh strands. The gripping element may be attached to at least one of the mesh strands. The sealing member may comprise at least two membranes, the membranes sealingly connected along their perimeter. The device may also include a supply duct for supply of a fluid into a space between the membranes for inflating and deflating the device.

Another aspect of the present invention provides a method of measuring a length of an incision in a blood vessel. An intravascular sealing device is provided comprising a sealing member having a mesh material formed in a grid pattern and a gripping element operatively attached to the sealing member. The length of the incision is measured using the grid pattern.

Another aspect of the present invention provides an intravascular device. The device comprises a gripping element, including a channel formed therein, the channel operatively adapted to contain at least one thread therein, a sealing member operatively attached to an end of the channel; and at least one thread operatively attached to the sealing member so that a movement of the thread causes the sealing member to change configuration. The sealing member may include a mesh material. The mesh material may comprise a plurality of mesh strands. The thread may be attached to at least one of the mesh strands. The movement of the thread may be a pulling movement. The sealing member and the gripping element may be formed in one piece. The device may also include a rigid guide including a channel operatively adapted to receive the gripping element therein. A plurality of threads may be attached to the sealing member such that a movement of the threads causes the sealing member to change configuration. The sealing member may fold in a parachute configuration. The sealing member may change configuration to an insertion configuration for insertion into a blood vessel. The sealing member may change configuration to a sealing configuration. The sealing member may change configuration to an insertion configuration with a first movement of the thread and change configuration to a sealing configuration with a second movement of the thread. The sealing member may be inserted into the blood vessel in an insertion configuration and change configuration to a sealing configuration within the blood vessel.

Another aspect of the present invention provides a method of connecting two blood vessels. An intravascular device is provided having a sealing member including a mesh material; and a gripping element operatively attached to the sealing member. A recipient vessel is opened. The device is inserted into the recipient vessel in an insertion configuration. The configuration of the device is changed to a sealing configuration. The blood in the vessel is allowed to flow through the recipient vessel and past the device. A second vessel is partly attached near the opening in the recipient vessel. The device is removed from the opening. The second vessel is completely attached to the recipient vessel.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

BRIEF DESCRIPTION OF THE DRAWINGS

FIGS. 9a, 9b and 9c respectively show a transverse cross-sectional view and an axial cross-sectional view of an inflatable embodiment of the sealing device according to FIG. 1 in respectively an uninflated and in an inflated state, whereas

DETAILED DESCRIPTION OF THE PRESENTLY PREFERRED EMBODIMENTS

Figure 1:
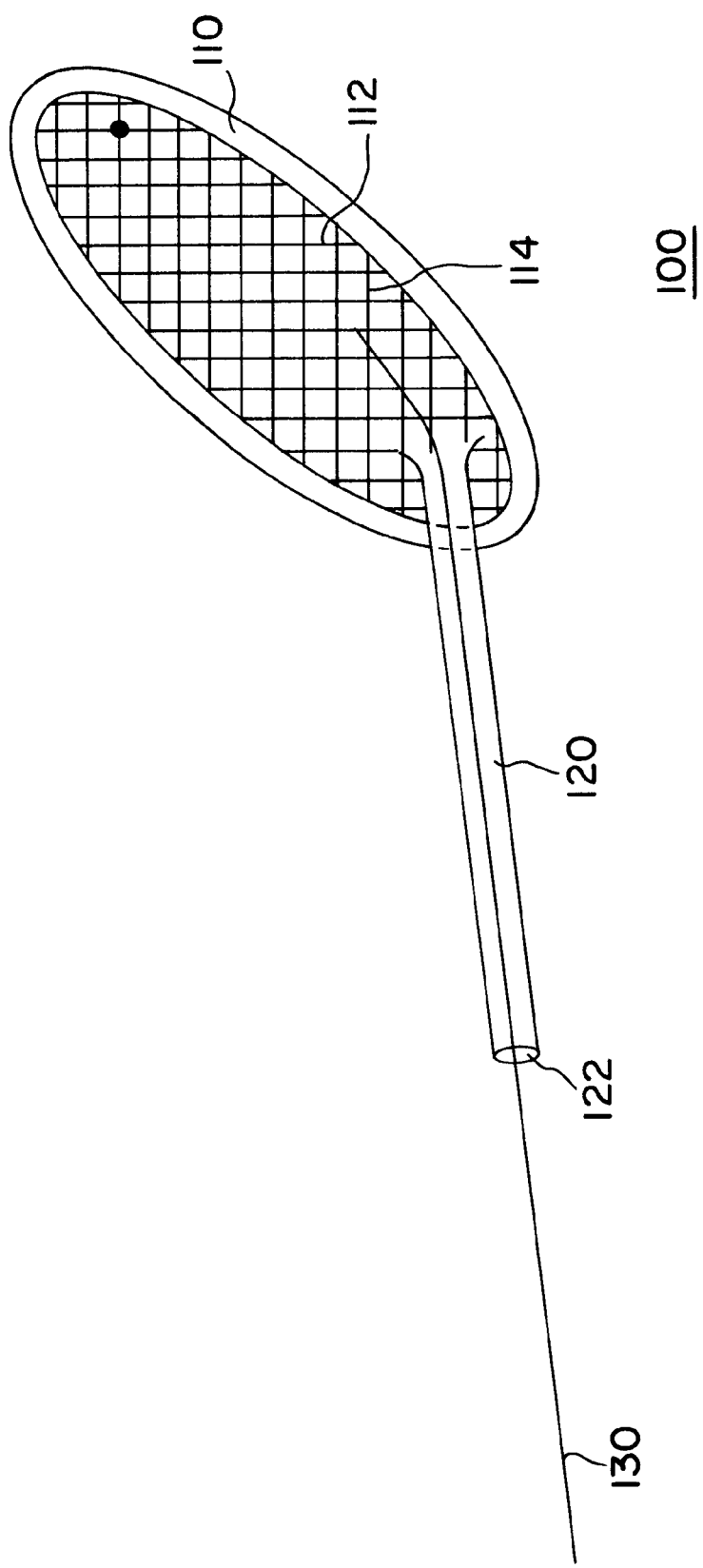
FIG. 1 shows a perspective view of an intravascular sealing device in accordance with the present invention.

FIG. 1 shows a temporary intravascular sealing device 100 in accordance with the present invention. Sealing device 100 may preferably include a seal 110 and a gripping element 120. Seal 110 may preferably include a mesh material 112. Gripping element 120 may preferably have a channel 122 formed within it. At least one thread 130 may preferably be contained within the channel of gripping element 120.

Preferably seal 110 may be made of a flexible sheet material that is preferably non-biodegradable. This material may be, for example, a polyurethane material, or other materials from which commercially available balloon catheters are manufactured. These materials may be available, for example, from Medtronic, Inc., Minneapolis, USA.

Seal 110 may also include a flexible, woven mesh 112 encapsulated within the material of the seal 110. The shape of the mesh 112 may contour the seal 100, leaving the outside surfaces of the seal 100 smooth. Alternatively, the mesh 112 could also be placed on the surface of the seal 100. Mesh 112 may preferably comprise a plurality of woven strands 114.

A gripping element 120, may be attached to seal 110. Gripping element may be a flexible tube 120 as shown in FIG. 1. Preferably, gripping element 120 may be attached to one or more of the woven strands 114 of the mesh 112. This may enhance the attachment of gripping element. Gripping element 120 may also be attached to seal 110. Gripping element 120 may also be formed integrally with seal 110. Gripping element 120 may also be attached to mesh 112 or seal 110 using, for example, an adhesive or solvent bond. Alternatively, gripping element 120 may be attached to one or more of the woven strands 114 of mesh 112 and then secured using an adhesive or solvent bond.

Alternatively, thread 130 may serve as a gripping element. Thread 130 may be attached to one or more of the woven strands 114 of the mesh 112. This may enhance the attachment of thread 130. Thread 130 may also be attached to seal 110. Thread 130 may also be formed integrally with seal 110. Thread 130 may also be attached to mesh 112 or seal 110 using, for example, an adhesive or solvent bond. Alternatively, thread 130 may be attached to one or more of the woven strands 114 of mesh 112 and then secured using an adhesive or solvent bond.

The seal 110 may then be inserted into a vessel by means of an insertion tool or general surgical tools. Seal 110 may then remain in the vessel until the anastomosis is complete. The pattern of the mesh strands 114 may create a grid pattern. Once the seal 110 is in place within the vessel, the grid may be used as a guide to measure the length of the incision (arteriotomy) in the vessel.

Figure 2:
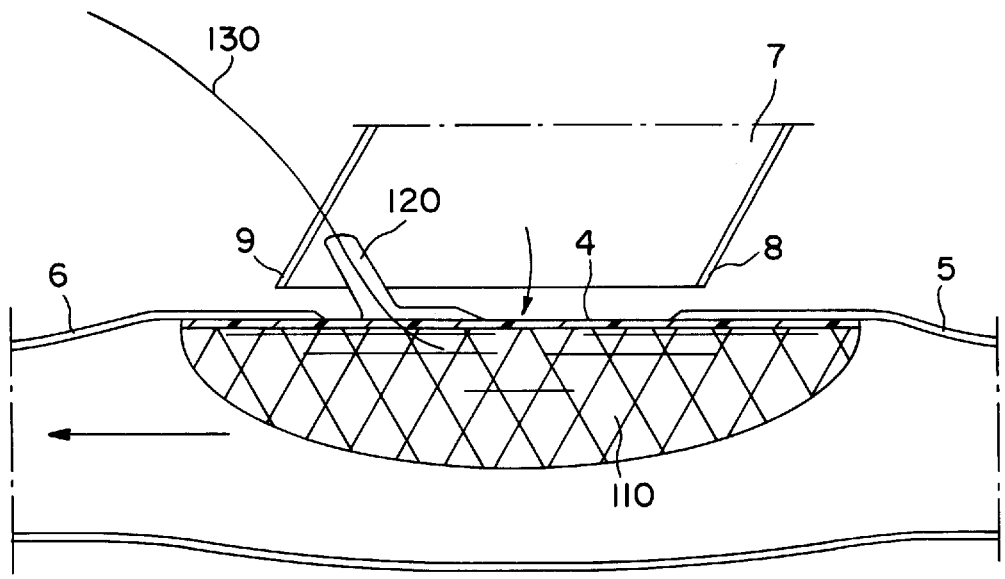
FIG. 2 shows the sealing device according to FIG. 1 placed in an axial cross-sectional view of a recipient vessel.

FIG. 2 shows the seal 110 being introduced into a recipient vessel. The seal 110 can be manipulated with gripping element 120 during insertion for positioning the seal 110 correctly inside the vessel. Gripping element 120 may also be used for retrieval of seal 110. For properly orienting the seal 110, orientation markings, for instance a grid structure, may be applied on the seal surface. Alternatively, the arrangement of mesh strands 114 may be used for properly orienting the seal 110. To minimize the risk of spontaneous inadvertent expulsion of the seal, the stiffness of the material of seal 110 may be greater in the length direction than in the width direction.

The seal 110 is introduced into a recipient vessel 6 through an opening 4 (arteriotomy) in the vessel wall 5. The seal 110 provides a leakage tight occlusion of the opening 4, allowing attachment of the donor vessel 7 around the edges of the opening 4 with a heel 8 and toe 9 as indicated.

Figure 3:
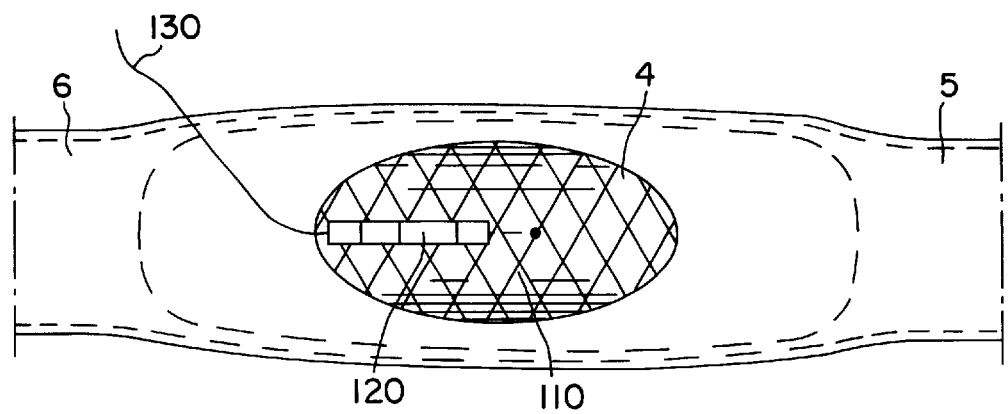
FIG. 3 shows a plan view of the sealing device according to FIG. 1.
Figure 4:
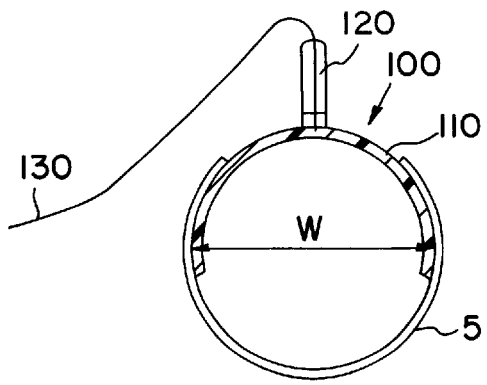
FIG. 4 shows a transverse cross-sectional view of the sealing device according to FIG. I in a recipient vessel.

As is shown in FIG. 3, a linear incision in the vessel wall will open into an elliptical opening 4 due to the tension in the elastic wall. The material of the seal 110 is sufficiently flexible such that its width dimensions, which are indicated as W in FIG. 4, can be made sufficiently small by folding to fit through opening 4 upon insertion and upon retrieval. After introduction into the vessel, the blood pressure will sealingly engage seal 110 with the inside of the wall of the vessel in the vicinity of the opening 4. Once in the proper place, the transmural pressure in the vessel will keep the extremely thin seal 110 neatly opposed to the inner arterial wall, thereby sealing the arteriotomy, even in the case of (atherosclerotic) luminal wall surface irregularities. At the positioning of the opening 4, the cross-sectional area of the vessel will slightly increase due to expansion of the vessel after making the incision, such that the introduction of the seal 110 does not impede the blood flow through the vessel.

Figure 5:
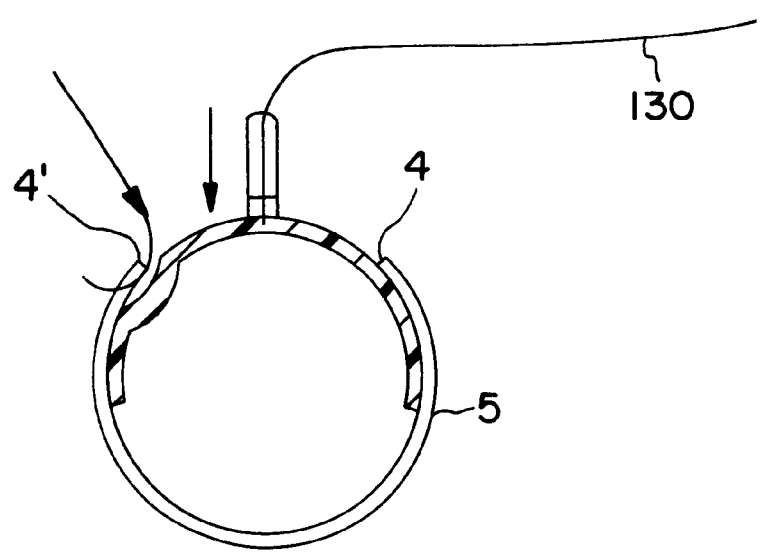
FIG. 5 shows the functioning of the sealing device according to FIG. 1 during suturing along the edge of an opening in the wall of a recipient vessel.
Figure 6:
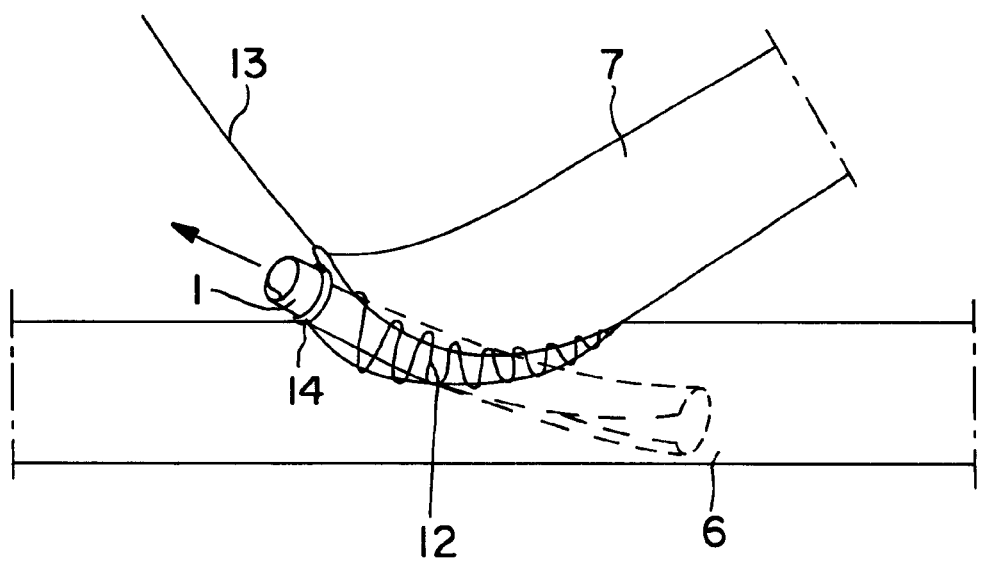
FIG. 6 shows a schematic perspective view of the retrieval of the sealing device according to FIG. 1 from a recipient vessel, FIGS. 7a to 7c respectively show a top view, a side view and a cross-sectional view along the line c—c in FIG. 7b of the sealing device according to FIG. 1.

As can be seen in FIG. 5, the seal 110 will flex and give way when a needle 11 is stuck from inside to outside through the edge 4' of the walls of the vessel near the opening 4 while still maintaining a liquid tight barrier preventing blood from exiting from the vessel through opening 4.

As shown in FIG. 5, the seal 110 may be removed from the vessel when a suture or sutures 12 around the perimeter of the opening 4 has been completed, but not tightened. The seal 110 may be pulled out of the vessel by grasping gripping element 120. Gripping element 120 may be grasped, for example, with a forceps or by hand. Alternatively, the seal 110 may be pulled out of the vessel by grasping thread 130. Suture 12 is then tightened to secure the bypass graft 7 to the recipient vessel 6. Upon insertion (as well as upon retrieval) a sleeve 14 may be used around the seal 1, for easy insertion (and retrieval).

Figure 7A:
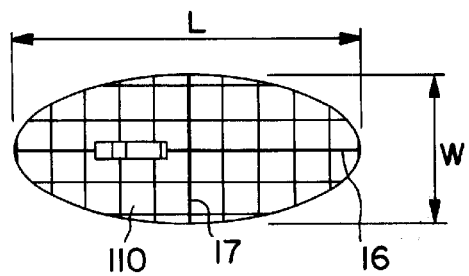
Figure 7B:
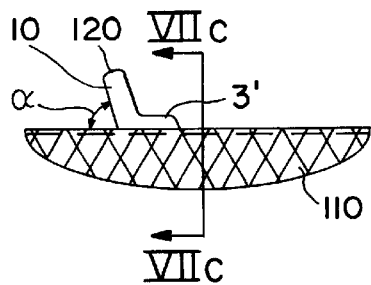
Figure 7C:
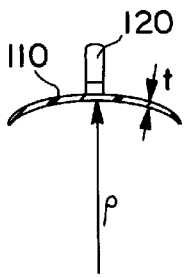

FIG. 7a shows a top view of the seal 110 according to the present invention having along its longitudinal axis 16 a length dimension, L, and a dimension in the width direction, W, along the transverse center line 17. Along the longitudinal center line 16, within the boundaries of the arteriotomy a ridge may be provided for manipulation purposes. As can be seen in FIG. 7b, the gripping element 120 may be placed at an angle á with respect to the outer surface of the seal 110. The gripping element 120 may be positioned eccentrically towards the toe of the anastomosis with its back edge 10 at a distance of about 2–4 mm from an edge of the seal 110. A ridge 3' may be provided for manipulation (rotation) of the seal 110 inside a vessel. As can be seen in FIG. 7c, the thickness t of the sheet material may be, for example, about 0.2 mm and the sheet material comprises a predisposed radius of curvature P. By providing a preformed curvature, the flexible seal 110 will easily fold in the width direction W that allows for easy insertion and retrieval through an opening in the vessel wall. On the other hand, the seal 110 has a natural tendency to unfold and oppose the vessel wall adjacent to the opening 4.

Figure 8:
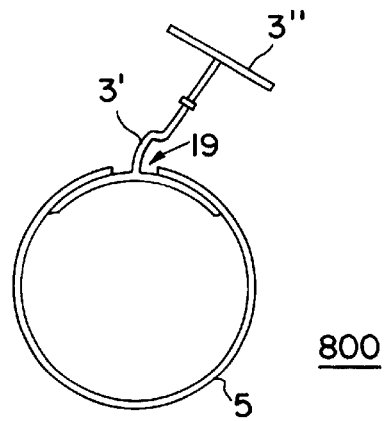
FIG. 8 shows a transverse cross-sectional view of a sealing device according to FIG. 1.

FIG. 8 shows another embodiment of the device 800 according to the present invention. In this embodiment seal 19 may be an inflatable body, for instance, two membranes that may be sealingly connected along their perimeter and including a supply duct for supply of a fluid into the space between the membranes for inflating and deflating the device. The luminal membrane is made of a stiffer material to keep the space between both membranes exceedingly small. In this way, the expansion of the seal in the width direction may take place by inflation. By deflating the seal, and for instance creating a slight vacuum inside, the dimension of the seal can be reduced significantly for easy insertion into and retrieval from the vessel. The supply duct may also end in an opening in the flexible sheet material for administration of substances through the supply duct into the recipient blood vessel. This may be suitable for instance in performing a rescue blood perfusion during emergency coronary bypass grafting. The rescue blood perfusion pressure may preferably not exceed normal intra-coronary pressure in order to avoid inadvertently expelling the seal. The seal may be used in a non-rescue situation when contractile function of the distal myocardium is marginal.

Figure 9A:
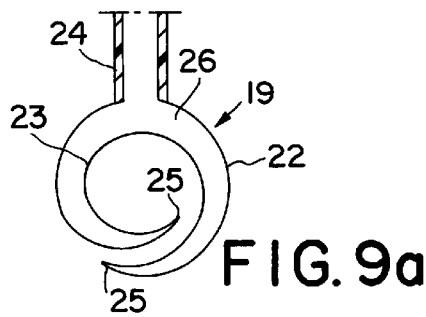
Figure 9B:
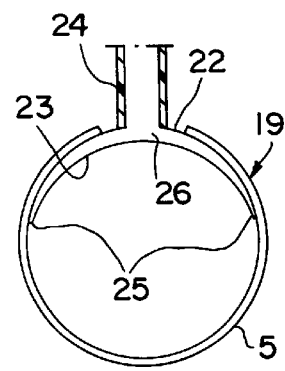
Figure 9C:
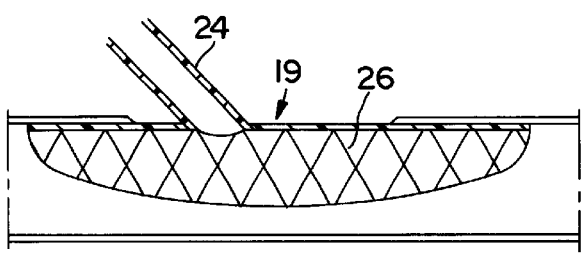

FIG. 9a shows an inflatable seal 19 according to an embodiment of the present invention in its partly deflated state. The inflatable seal 19 comprises an inflatable element 26 having two membranes 22, 23, which are sealed along their perimeter 25. The membranes 22,23 are connected to a supply duct 24 by which a fluid, for instance saline, can be introduced between the membranes 22,23. Hereby the inflatable element 26 of the seal 19 assumes its inflated position as shown in FIG. 9b. The membrane 22 is relatively compliant and opposes the wall 5. Luminal membrane 23 is relatively stiff. In the inflated state, the distance between membrane 22 and membrane 23 may be minimal to create a minimal cross-sectional area (obstruction to flow). In a completely deflated state (active suction), membranes 22 and 23 touch each other. By their pre-formed molding, deflation results in resumption of the original folded state, which by its small size allows easy insertion and retrieval. FIG. 9c shows an axial cross-sectional view of the device 19 of FIGS. 9a and 9b. Depending on the inflation pressure the inflatable seal adjusts to the radius of curvature of the artery and seals the arteriotomy. Similar to the non-inflatable device, its canal and balloon skin material are non-thrombogenic (possibly heparin or other anti-coagulation compound coated), atraumatic and possibly hydrophilic (c.f. glide wire). The balloon skin 22 is compliant, such that the suture needle can follow its regular course from inside to outside without producing a leak. The balloon skin gives way to the needle if the needle point is not positioned perpendicularly to the inflatable seal's skin.

With the ultrathin skin and limited size of the inflatable seal 19, three objectives may be satisfied: (1) minimal decrease in cross-sectional area of the recipient artery lumen and hence, minimal obstruction to flow; (2) minimal wall damage by the intravascular device; (3) by not covering the entire circumference as by e.g. an intracoronary canal shunt, the entrance to side branches is not blocked. The absence of circumferential injury may accelerate re-endothelialization by spread of endothelial cells from the side of the artery opposite to the arteriotomy, rather than from minute side branches (vasa vasorum) and the proximal and distal, non-occluded segments. The former is a shorter distance. Smooth muscle cells are not injured. The minimal intimal hyperplasia response is similar to healing after conventional suturing. The lumen of the inflatable seal 19 is minimal to reduce the arterial lumen least. The seal 19 has a preformed shape, which fits the size of the artery. In the deflated state, the seal takes the shape depicted in FIG. 9a. The luminal side of the seal is made of a balloon skin, which has the property that it takes on the depicted shape. The curling should be as tight as possible to obtain the lowest profile in cross-section. The seal is inflated by saline. The inflation pressure is monitored. Inflation pressure is determined empirically. Inflating the seal 19 will de-curl the seal. A further increase in inflation pressure will stretch it. Little inflation pressure suffices to keep the seal in its proper shape and position. By increasing the pressure in the inflatable seal, it extends more laterally and it becomes more stiff. In this condition, more traction can be exerted on its attachment, if needed, before it slips out of the arteriotomy. It might be useful, for example, to exert some traction to lift the artery a little out of its bed. By decreasing the pressure, the seal takes on its more deflated, curled shape and becomes less stiff and may follow more the possibly irregular inner surface of the atherosclerotic artery. With very little inflation pressure it will probably seal perfectly due to the transmural pressure in the artery, once it has been positioned properly.

Figure 9D:
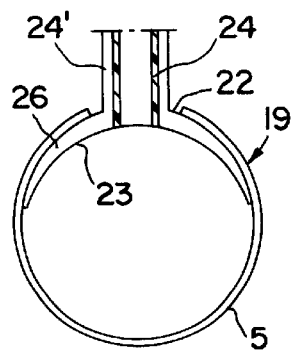
FIG. 9d shows a transverse cross-sectional view of an inflatable sealing device of the double lumen type.

FIG. 9d shows an inflatable seal 19 wherein the membrane 22 extends upwardly along the supply duct 24, to form a so-called double lumen canal having two ducts 24, 24'. The inflatable element 26 of the seal 19 can be inflated by means of duct 24'. Via central duct 24 blood perfusion can be carried out or drugs can be delivered to the vessel. The double lumen canal 24, 24, itself is also used as a cord to insert, manipulate and retrieve the seal.

The principle depicted in FIGS. 9a–9d implies that one seal may fit different sizes arteries within a certain range, e.g. for coronary artery bypass grafting. In an artery that is relatively small in relation to the seal, however, the device may become flow limiting. For femoral artery bypass grafting, obviously a larger size seal is required.

The inflatable seal may be positioned in either two ways: (1) through the arteriotomy, or (2) via an introducer sheath that has been positioned in the recipient artery. The second method is similar to inserting a catheter into an artery via an introducer. The introducer with needle may be inserted into the lumen of the recipient artery. The needle is withdrawn and the seal is inserted in deflated and low profile state like a balloon catheter into the lumen. Next, the introducer is removed over the supply canal of the seal.

The seal 19 may be inserted through a sheath. After inflation the puncture site can be enlarged to a full size arteriotomy by hooked scissors, taking care not to puncture the balloon skin of the seal. Again, the seal 19 will give way to the lower jaw of the scissors without causing a leak.

The supply canal of the seal may have two and possibly four functions: (1) a card to insert, manipulate and retrieve the seal; (2) inflation/deflation channel of the seal; (3) channel for local drug delivery; and (4) rescue blood perfusion. If the inflatable element 26 of the seal 19 is made of balloon material with microscopic pores, the seal can function as local drug delivery device. For example, local heparin delivery reduces the risk of clot formation and inhibits local intimal hyperplasia as vessel wall repair response to vascular surgery injury. The local delivery of heparin may reduce or even abolish the need for anti-coagulation during anastomosis suturing. Obviating the need for systemic anti-platelet therapy and anticoagulation will contribute to reducing bleeding problems.

After deflation of the seal, it resumes its low profile shape, which facilitates its removal through a small residual opening in the anastomosis. At this stage, all stitches have been made, but the running suture wire has not yet been fastened. During retrieval and removal, some bleeding will occur which will stop as soon as the suture wire loops are picked up and the wire is tied.

Figure 10:
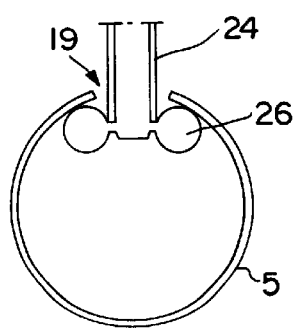
FIG. 10 shows a further embodiment of an inflatable sealing device according to FIG. 1.

FIG. 10 shows an embodiment particularly suitable for the proximal anastomosis on the aorta, in which the sealing device 19 comprises a dough-nut-shaped inflatable element 26.

Figure 11:
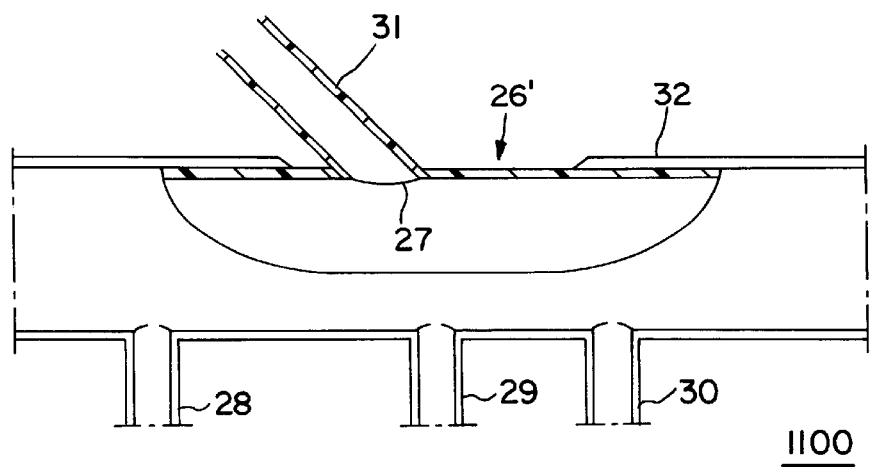
FIG. 11 shows an axial cross-sectional view of a sealing device according to FIG. 1 suitable for emergency perfusion.

FIG. 11, shows a non-inflatable sealing device 1100 for use in rescue arterial perfusion. In this embodiment similar to FIG. 1, the seal 32 comprises an opening 27, which is in fluid communication with a supply canal or duct 31 for blood supply. The supply canal 31 can be fed either directly from the arterial tree or via a pump. The supply canal of the seal may have three functions: (1) a cord to insert, manipulate and retrieve the seal; (2) channel for blood perfusion; (3) channel for delivery of drugs. By use of this seal 32, according to the present invention all side branches 28 and 29 and 30 can also be supplied with blood. In this embodiment the sheet material of the seal need not have a preformed curvature in the width direction, when the flexible sheet material is sufficiently flexible to conform to the curvature of the wall of the vessel. However for easy retrieval and increased sealing properties, a preformed curvature in the width direction is preferred.

Figure 12:
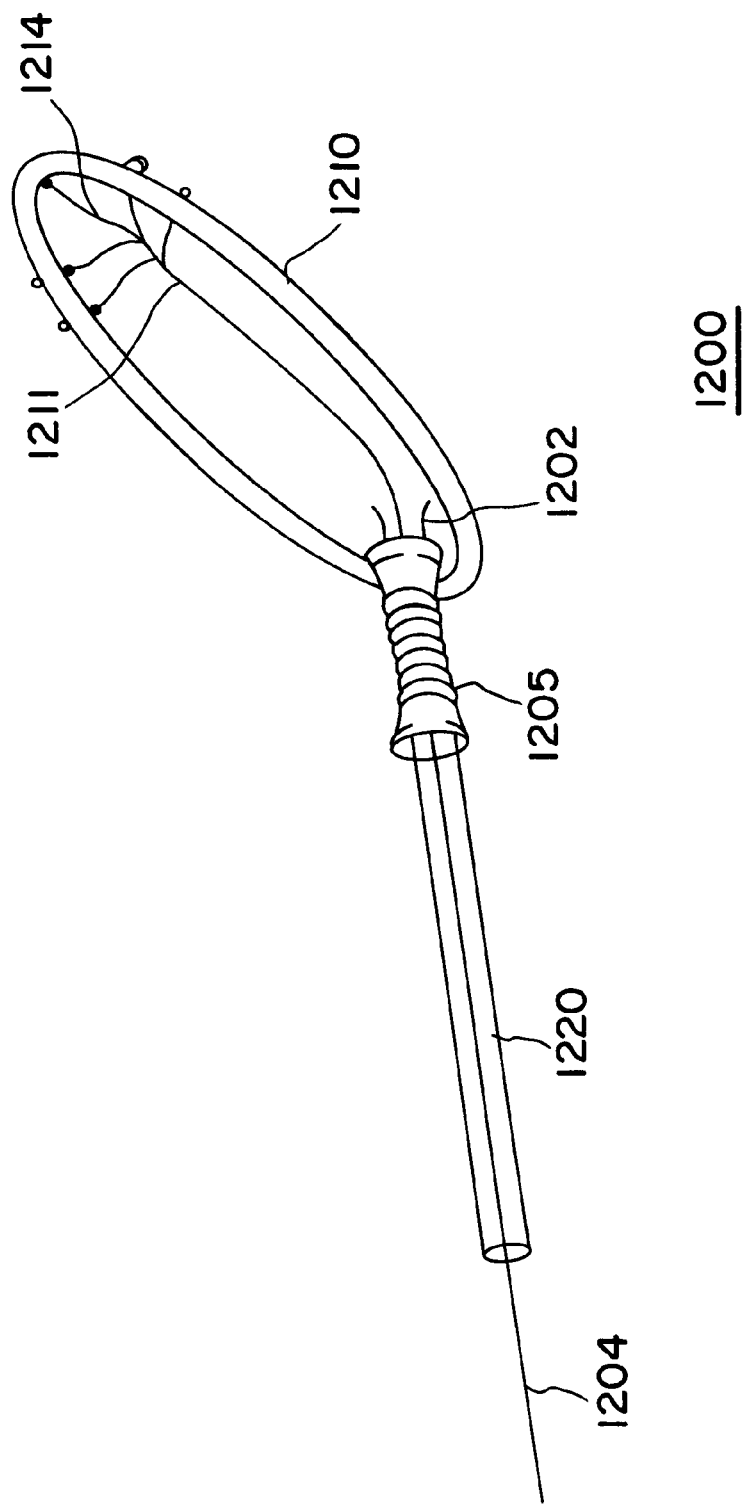
FIG. 12 shows another embodiment of a reinforced mesh intravascular sealing device in accordance with the present invention.

FIG. 12 shows another embodiment of the sealing device 1200 of the present invention.

Device 1200 may include a hollow tube 1220 that has one end protruding completely through the seal 1210 from the top side of the seal to the under side. Preferably tube 1220 is made of a flexible, stretchable material, which is preferably non-biodegradable. This material may be, for example, a polyurethane material, or other materials from which commercially available balloon catheters are manufactured. These materials may be available, for example, from Medtronic, Inc., Minneapolis, USA. Preferably, tube 1220 and seal 1210 may be formed of the same material. Tube 1220 and seal 1210 may be formed as a unit. Alternatively, tube 1220 and seal 1210 may be made as separate pieces and adhered together using any suitable adhesive means. The point 1202 at which the outer diameter of tube 1220 meets the top surface of the seal 210 may be sealed. This point 1202 may be offset from the center point of the seal 1210, along the symmetrical plane towards the distal portion of the seal.

At least one thread 1204 may be fixed to the distal portion of the seal 1210 at point 1211. Preferably thread 1204 is made of a material such as braided Dacron or a typical suture material. Such material may be, for example, a smooth, matte finish polyurethane that is tear-resistant and impervious to blood. The suture material may be translucent or transparent to allow visibility, or may alternatively be colored. Seal 1210 and tube 1220 may be constructed of a soft plastic, which may be translucent, transparent or colored.

Preferably, seal 1210, tube 1220 and thread 1204 are made of biocompatible materials. A biocompatible material prompts little allergenic response from the patient's body and is resistant to corrosion from being placed within the patient's body. Furthermore, the biocompatible material preferably does not cause any additional stress to the patient's body; for example, it does not scrape detrimentally against any elements within the vessel.

Preferably thread 1204 may be fixed to the under side of the seal 1210 so as to keep the top side of the seal smooth. Thread 1204 may be drawn up through the inner diameter of the stretchable tube from the underside of the sheet. The length of the thread 1204 may be longer that the length of the tube 1220 so that thread 1204 may extend past the top end of the tube 1220. The inner diameter of the tube 1220, containing the thread 1204, may then be sealed off at some point between the tube and sheet joint and the top end of the tube. However, the thread 1204 within the tube 1220 may move freely between its two fix points.

Device 1200 may also include a gripping guide 1205. This gripping guide, may be for example a rigid tube 1205. The free end of the thread may then be threaded through tube 1205. Preferably tube 1205 may be made of a rigid material such as plastic. The rigid tube 1205 may be positioned next to the top surface of the seal 1210. By pulling the thread taut and keeping the rigid tube 1205 in place, the stretchable tube 1220 may pull the thread 1204. Stretchable tube 1220 may thereby also pull the portion of the seal 1210 to which the thread 1204 is attached at point 1211. Pulling the thread taut at point 1211 puts it into a collapsed configuration suitable for insertion. Rigid tube 1205 may be used to allow better gripping of the device 1200. Once inserted, thread 1204 may be released. Seal 1210 may be allowed to relax to its original position. The number of threads and the fixed locations of the threads on the seal 1210 can vary in order to fold the distal portion of the seal 1210 at different focal points. For example, in the "parachute" embodiment shown, the thread ends 1214 of thread 1204 can be different lengths such that the folding of the seal 1210 along the alternate axes occurs at staggered times. For example, if the thread to the distal tip of the seal 1210 was shorter than the thread to the sides, then the distal tip would preferentially fold before the sides. When the thread 204 (and thread ends 1214) are pulled taut, the seal collapses like a closed parachute for insertion into the vessel.

Alternatively, an element may be attached to the seal to help fold the seal. These include pulling the seal 1210 into an oval, beveled tube by grasping an element attached to the sheet, such as a thread or bonded protrusion.

The seal 1210 may be difficult to place into the vessel with forceps alone because it may tend to return to its original shape. This tendency may cause the seal 1210 to eject from the vessel during insertion. The distal end of the seal 1210 may be the last portion of the seal 1210 to be placed into the vessel. The tendency of seal 1210 to return to its original shape may make it difficult to place into the vessel without damaging the vessel. A new user may take a long time in placing seal 1210, which may be undesirable under surgery time constraints.

Device 1200 may allow the distal end of seal 1210 to be folded underneath itself during the insertion phase. Once the seal 1210 is completely inside the vessel, device 1200 may allow the seal 1210 to return to its original shape and assume its sealing configuration inside the vessel.

During retrieval, seal 1210 must often be pulled through a confined area, such as in a nearly completed anastomosis. Device 1200 may fold seal 1210, so retrieval may be is less traumatic to the vessel and less difficult.

Such a device 1200 provides an intravascular arteriotomy seal 1210, which can be easily inserted into and retrieved from a donor or recipient vessel. During insertion into a recipient artery, occlusion of the artery is required only for a brief moment or is not required at all when intravascular pressure is low. When the seal 1210 according to the invention is in place, the blood flow in the opened artery can be resumed and the distal end of the bypass graft can be grafted onto the opening of the recipient vessel without leakage of blood along the seal.

Prior to completion of the bonding, such as by tightening (securing) the sutures which connect the bypass graft to the recipient vessel, the seal 1210 of device 1200 can be withdrawn from the opening in the recipient vessel wherein the device will easily bend in the width direction by contact with the sides of the opening in the vessel wall, due to its flexibility and preformed curvature in the width direction. Thereafter, the sutures can be tightened and the grafting can be completed.

With seal 1210, only a very short or no occlusion of the blood vessel upon insertion or retrieval may be required. Once properly positioned, the seal 1210 provides a bloodless arteriotomy for precise (microsurgical) anastomosis suturing without interfering with recipient artery blood flow, with minimal damage to the wall of the vessel and without blocking of any side branches in the vessel. Seal 1210 may be particularly useful for coronary artery bypass grafting on the beating heart, such as for instance described in PCT publication WO 97/10753, herein incorporated by reference. Because the sheet material of the seal according to the present invention has a preformed curvature in the width direction, the material will have a natural tendency to fold easily in the width direction. Hereby the seal 1210 can be easily retrieved through the insertion opening by pulling.

The sealing device of the present invention may be beneficial in a number of different uses, and in a variety of surgical procedures. Some examples of such uses and procedures are provided below.

Bypass Grafting

To provide adequate blood supply to an organ or tissue with impaired blood supply, the end of an extra vessel (bypass graft) is connected end-to-side or side-to-side to the recipient artery downstream of the obstruction in the recipient artery.

To establish this connection, i.e. the distal anastomosis, blood flow in the recipient artery is interrupted by, for example, temporary ligation or clamping of the artery proximal and distal of the connection site. Once the blood flow is interrupted, the recipient artery is opened (arteriotomy). Next, the exit (distal end) of the bypass graft is connected by suturing (or other bonding method) to the recipient artery.

This is achieved by suturing the inside of the bypass graft to the inside of the recipient artery. The rationale of this precise anastomosis suturing is that the inner lining of the vessels (the endothelial layer) is anti-thrombogenic, whereas the outer layer is highly thrombogenic. Thrombosis at the transition of donor to recipient vessel reduces the cross-sectional area of the lumen at the anastomosis and hence jeopardizes the quality of the distal anastomosis.

Narrowing (stenosis) of the anastomosis limits the maximum blood flow through the bypass graft.

In a proximal anastomosis, the entrance (proximal end) of the bypass graft needs to be connected to an artery, which serves as pressure source of oxygenated blood. If a natural artery can serve as bypass graft, like e.g. the internal mammary artery in coronary artery bypass grafting, only the distal anastomosis needs to be made. Sometimes, however, the internal mammary artery is used as free graft or the radial artery is used as arterial conduit and a proximal anastomosis has to be made. Venous bypass grafts always require a proximal anastomosis, because their transformation to an arterial conduit requires connection to a source of arterial blood. Similar to suturing the distal anastomosis of the bypass graft, suturing the proximal anastomosis requires interruption of the source blood flow in the vicinity of the proximal anastomosis site.

Interruption of Blood Flow in Vascular Surgery: Adverse Effects

Currently, all vascular surgery is performed during interrupted blood flow in the vicinity of the anastomosis, because suturing (or otherwise bonding the vessel edges) requires a bloodless surgical field for proper exposure of the vessel edges. The bloodless field, however, is obtained at a price.

Temporary interruption of blood flow has potentially a number of adverse effects. First, interruption of existing residual flow through high grade stenosis or, when the artery is proximally totally occluded, interruption of collateral flow to the end-organ may impair its function (ischemic dysfunction). Second, it may jeopardize the end-organ's cellular integrity (ischemic injury). Third, re-establishment of blood flow after cessation of flow may lead to reperfusion injury and dysfunction. Fourth, during the period of completely interrupted flow, in ischemic tissues noxious metabolites accumulate. The abrupt release into the circulation of accumulated noxious metabolites from the reperfused area may cause adverse effects elsewhere.

Vascular surgeons limit the period of flow interruption as much as possible by performing bypass surgery as fast as possible. This requires (a) a still surgical field, (b) absence of blood which obscures the vessel edges, and (c) experience, concentration and manual dexterity. The distal anastomosis requires meticulous placement of the needle into the edge of the recipient artery entrance (arteriotomy). If the stitch is too close to the edge, there is the risk of wall tissue tearing by the suture wire. If the stitch is too far from the edge, there is the risk of creating a tissue flap in the lumen of the anastomosis with subsequent risk of suture line mural thrombosis and suboptimal anastomosis quality.

The present invention obviates the need to interrupt flow in the recipient artery or limits it to less than about 2 minutes, a period which is not expected to lead to adverse effects.

Coronary Bypass Grafting

Recently, coronary artery bypass grafting on the beating heart has regained interest. Coronary motion can now be restrained adequately with a mechanical stabilization device such as, for example the Octopus device from Medtronic, Inc. Interruption of the coronary flow, however, in the segment of the recipient artery to be grafted may result in regional myocardial ischemia with ischemic ECG changes, loss of regional contractile function and hence, impaired cardiac pump function. Ischemia may induce conduction disturbances. In addition, inhomogeneous perfusion of the myocardium may create vulnerability to arrhythmias. Changes in rate or rhythm may impair pump function. Reperfusion may cause myocardial cell injury ("reperfusion injury") and induce ventricular fibrillation, which causes immediate cessation of all pumping action.

However, due to usually well-established collateral circulation in patients that require coronary bypass grafting for stable angina, flow interruption for 10–20 minutes is remarkably well tolerated without plasma CPK-MB rise indicative of myocardial cell death. In unstable angina, in contrast, adequate collateral circulation is likely to be absent and coronary flow interruption during emergency coronary surgery on the beating heart may further damage the jeopardized myocardium.

Collateral Coronary Flow

In the normal heart, perforating side branches of the epicardial coronary artery feed the underlying myocardium. In case of a proximal occlusion, there is (limited) flow in these perforating branches, albeit in the reverse direction (collateral flow). The sources of the collateral flow are tiny interconnections with nearby unobstructed branches of the arterial coronary tree. In patients with stable angina pectoris the collateral flow usually has sufficient capacity to provide the flow through the main epicardial conduit needed for the heart during resting conditions. During exercise, however, blood supply becomes insufficient and the patient experiences cardiac ischemia (angina pectoris). Since the lesion progression from flow limiting to totally occlusive atherosclerotic obstruction takes many years, collateral circulation has had ample time to develop by expanding the originally minute interconnections between branches of the coronary tree.

In elective coronary bypass grafting for stable angina owing to a proximal coronary occlusion, the well-developed collateral circulation generally allows clamping and isolating of the mid-segment of the coronary artery for creation of the distal bypass connection. However, the consequences of temporary occlusion of the recipient artery proximal and distal of the anastomosis site are unpredictable, because very small arteries cannot be visualized pre-operatively by angiography. Distal clamping of a proximally occluded artery may produce myocardial ischemia in the distal perfusion area, because collateral flow in the epicardial conduit is blocked in the antegrade direction. In addition, clamping or ligating the coronary artery may also block retrograde collateral flow in the epicardial conduit from a more distal side branch to a more proximal side branch which supplies a region which happens to lack adequate collateral flow.

Sometimes, the coronary flow interruption is not tolerated and the pumping function of the heart deteriorates. One remedy is to restore the blood flow and convert the procedure to conventional coronary bypass grafting using the heart lung machine. If the coronary artery has already been opened, emergency conversion becomes necessary. Another remedy is to insert an intra-coronary shunt canal. The present invention prevents ischemic problems and hence, obviates stand-by of the heart lung machine.

Dry Surgical Field

To perform precise coronary bypass surgery, a good view of the arteriotomy edges is required. The presence of blood hampers suturing.

Ample collateral flow via perforating branches that happen to be located in the occluded coronary segment produces retrograde flow that wells up in the arteriotomy, obscures its edges and jeopardizes the quality of the anastomosis.

The present invention restores the dry surgical field and allows conventional anastomosis suturing without leakage of blood owing to the flexibility of the sealing sheet. In the standard, conventional bypass surgery, the heart is arrested by perfusion of the coronary arteries with, in general, a cold cardioplegic crystalline solution, which provides a perfectly clear, view on the arteriotomy edges.

However, when for example the heart muscle is protected by retrograde blood cardioplegia, the same obscuring effect of blood hampers the anastomosis suturing and the present invention may provide a dry surgical field in spite of the blood cardioplegia. Thus, a useful additional benefit of the temporary luminal arteriotomy seal is the creation of a dry surgical field with unimpaired view on the arteriotomy edges for meticulate anastomosis suturing.

Obstruction to Flow

With the intravascular seal and method of using said seal according to the present invention, which seal may for instance be made of polyurethane of a thickness of about 0.2 mm, a minimal or no decrease in cross-sectional area of the recipient artery lumen is achieved, resulting in a minimal or no obstruction to flow.

Vessel Wall Injury

The major concern with any device inserted in an artery is its potential for wall injury, because intra-arterial injury to the wall may lead to local luminal narrowing due to acute mural thrombosis and/or formation of intimal hyperplasia (scar tissue). As the device according to the present invention will only contact a part of the vessel wall circumference, endothelial damage by the intravascular device of the present invention is minimized. Furthermore, if it has damaged or removed endothelium, re-endothelialization is accelerated owing to the presence of undisturbed endothelium at the opposite side of the arteriotomy. In addition, by only covering a limited part of the inner circumference of the vessel with the seal according to the invention, the entrance to side branches remains open during bypass grafting.

Proximal Anastomosis

One major objective of coronary bypass graft (CABG) surgery on the beating heart is to avoid adverse cerebral effects, which occur in 6% of cases. These serious adverse effects are attributed for about 50% to relatively large emboli generated by manipulation of the ascending aorta and for about 50% to relatively small emboli generated by the use of the heart-lung machine, in combination with low arterial pressure.

In the CABG patient, the ascending aorta is usually atherosclerotic as well. Any manipulation of the atherosclerotic ascending aorta may dislodge particulate, atherosclerotic or thrombotic emboli from the aortic wall. These emboli may block the (micro)circulation anywhere in the body, but if an embolus follows the bloodstream to the brain, the consequences may be particularly serious.

In conventional CABG using the heart-lung machine and cardioplegic cardiac arrest, the ascending aorta has to be cross-clamped. Off pump, beating heart CABG obviates the need to cross-clamp the ascending aorta. Currently, however, virtually all vein grafts are connected at their proximal end to the ascending aorta as source of pressurized oxygenated blood. Each time a side clamp is applied to create a dry surgical field, there is the risk of dislodging particulate emboli.

A slight modification of the earlier described arteriotomy seal according to the present invention, to be used for the distal anastomosis, will obviate the need to apply a side-clamp on the (ascending) aorta for creating the proximal anastomosis of a vein graft or a free arterial graft.

In addition, side-clamping the ascending aorta in an off-pump beating heart CABG patient will locally reduce the cross-sectional luminal area, and hence, will increase resistance to flow. Both the ensuing increased arterial pressure in the ascending aorta proximal to the side-clamp (increased afterload for the left ventricle) and the decreased arterial blood pressure beyond the side-clamp (decreased perfusion pressure for the brain and other tissues) are unwanted side effects.

Thus, obviating the need for the aortic side-clamp is useful both in off-pump CABG and in conventional CABG using the heart-lung machine. Conceptually, the device for the proximal anastomosis on the ascending aorta is the same as for the distal anastomosis, but the embodiment is slightly different. First, the hole in the aorta is not created by a longitudinal incision, but by punching a round hole (3–4 mm in diameter). Second, the dimensions of the seal conform to the ascending aorta with an internal diameter 25–30 mm and wall . thickness 1 mm. Thus, the umbilical cord/inflation channel canal inserts in the middle of the seal. Fourth, the seal is oval or round. Fifth, the inflatable embodiment may be a torus as well ("dough-nut").

It is contemplated that the seal of the present invention may be used in a variety of procedures in addition to those described above. It should be appreciated that the embodiments described above are to be considered in all respects only illustrative and not restrictive. The scope of the invention is indicated by the following claims rather than by the foregoing description. All changes that come within the meaning and range of equivalents are to be embraced within their scope.

We claim:

1. A medical device for insertion through an opening in a wall of a blood vessel, comprising:

a flexible, elongated gripping element, including a channel formed therein;

a rigid guide including a guide channel receiving the gripping element therein such that a first portion of the gripping element is received within the guide channel and a second portion of the gripping element extends from the guide channel at a proximal end thereof;

a thin sealing member adapted to conform to an interior portion of the wall of the blood vessel without obstructing the blood vessel and operatively attached to an end of the gripping element; and at least one thread extending through the channel of the gripping element such that a portion of the thread extends from the channel of the gripping element at a proximal end thereof, the thread also operatively attached to the sealing member so that the sealing member collapses as the thread is pulled taut at a point proximal to the rigid guide.

2. The device of claim 1 wherein the sealing member has an oval shape.

3. The device of claim 1 wherein the sealing member is curled to facilitate insertion into the blood vessel.

4. The device of claim 1 wherein the sealing member is thinner near its perimeter than near its center.

5. The device of claim 1 wherein the sealing member has increased stiffness along its length.

6. The device of claim 1 wherein the sealing member is made of a non-biodegradable material.

7. The device of claim 1 wherein the sealing member is made of a deformable sealing material.

8. The device of claim 1 wherein the sealing member comprises at least two membranes, the membranes sealingly connected along their perimeter.

9. The device of claim 8 further comprising:

a supply duct for supply of a fluid into a space between the membranes for inflating and deflating the device.

10. The device of claim 1 wherein the sealing member includes a mesh material.

11. The device of claim 10 wherein the mesh material forms a grid pattern.

12. The device of claim 10 wherein the mesh material comprises a plurality of mesh strands.

13. The device of claim 12 wherein the thread is attached to at least one of the mesh strands.

14. The device of claim 1 wherein the sealing member and the gripping element are formed in one piece.

15. The device of claim 1 wherein the sealing member collapses in a parachute configuration.

16. The device of claim 1 wherein the sealing member collapses to an insertion configuration for insertion into a blood vessel.

17. The device of claim 1 wherein the sealing member changes configuration to a sealing configuration by releasing tension on the thread.

* * * * *